United States Patent

Knothe et al.

[11] Patent Number: 6,143,031
[45] Date of Patent: Nov. 7, 2000

[54] INTERVERTEBRAL IMPLANT WITH COMPRESSIBLE SHAPED HOLLOW ELEMENT

[75] Inventors: Inga Knothe, Biel; Alfred Benoit, Lengnau, both of Switzerland

[73] Assignee: Synthes (U.S.A.), Paoli, Pa.

[21] Appl. No.: 09/051,770

[22] PCT Filed: Oct. 20, 1995

[86] PCT No.: PCT/CH95/00244

§ 371 Date: Apr. 20, 1998

§ 102(e) Date: Apr. 20, 1998

[87] PCT Pub. No.: WO97/15247

PCT Pub. Date: May 1, 1997

[51] Int. Cl.$^7$ ............................................. A61F 2/44
[52] U.S. Cl. ................................................ 623/17; 606/61
[58] Field of Search ........................ 623/17, 11; 606/61

[56] References Cited

U.S. PATENT DOCUMENTS

| | | | |
|---|---|---|---|
| 4,863,477 | 9/1989 | Monsoon | 623/17 |
| 5,458,642 | 10/1995 | Beer et al. | 623/17 |
| 5,554,191 | 9/1996 | Lahille et al. | 623/17 |
| 5,593,409 | 1/1997 | Michelson | 623/17 |
| 5,676,702 | 10/1997 | Ratron | 623/17 |
| 5,782,919 | 7/1998 | Zdeblick et al. | 623/17 |

FOREIGN PATENT DOCUMENTS

| | | |
|---|---|---|
| 0 664 994 A1 | 8/1995 | European Pat. Off. . |
| 40 12 622 C1 | 7/1991 | Germany . |

*Primary Examiner*—Michael J. Milano
*Assistant Examiner*—Choon P. Koh
*Attorney, Agent, or Firm*—Pennie & Edmonds LLP

[57] ABSTRACT

An intervertebral implant for fusion of vertebral bodies is disclosed. The implant includes a flattened shaped hollow element in the form of a hollow cylinder, hollow truncated cone, hollow truncated pyramid, or hollow truncated wedge, with an outer surface having a flattened upper bone-contact face, flattened lower bone contact face, and two lateral faces. The upper and lower bone-contact faces can be elastically compressed towards the interior space of the hollow element in such a way that the maximum distance between the upper and lower contact faces can be reduced by 0.5 to 5.0 mm. The compressibility of the implant allows the insertion of the implant without the need for distracting the vertebras. After the implant is implanted, the engagement of an engagement lip with an interlock means prevents the compression of the implant.

19 Claims, 1 Drawing Sheet

INTERVERTEBRAL IMPLANT WITH COMPRESSIBLE SHAPED HOLLOW ELEMENT

FIELD OF THE INVENTION

The invention refers to an intervertebral implant for fusion of vertebral bodies, particularly in the region of the lumbar part of the spinal column.

BACKGROUND

From the prior art there are already different types of such intervertebral implants known though which show the following disadvantages:

to insert the implant in the intervertebral space the respective vertebras must be expanded by means of suitable instruments; and the implant is endangered of sinking in the end plates of the respective vertebras.

SUMMARY OF THE INVENTION

The present invention relates to an intervertebral implant which is insertable into the cleaned out intervertebral space in a controllable manner without an expanding instrument.

The implant according to the present invention comprises a flattened shaped hollow element with an outer surface having a flattened upper bone-contact face, a flattened lower bone-contact face, and two lateral faces. The upper and the lower bone-contact faces are elastically compressible towards the interior space of the hollow element such that the maximum distance between the upper and the lower bone-contact face is reducible by 0.5–5.0 mm.

The flattened hollow element can have the shape of a hollow cylinder, hollow truncated cone, hollow truncated pyramid or hollow truncated wedge.

Dimensions, geometry and material should be chosen such, that the maximum distance H between upper and lower bone-contact face is reducible by 0.5–5.0 mm preferably 1–3 mm.

In case of application of a force of pressure of 12 Newton on the upper and lower bone-contact faces the maximum distance H shall be reducible by 15% to 30% preferably 20% to 25%. The compressibility of the implant allows its insertion without having to apply an expanding instrument.

Therewith the advantage is reachable that a minimum expenditure of force is necessary for the implantation and a controllable insertion of the compressed implant is possible. A minimum invasive and open surgery technique is therewith applicable.

The large bearing area of the implant prevents its sinking in into the end plates.

A preferred embodiment of the invention consists therein, that in the interior space of the hollow element an engagement lip is provided which is engageable into an interlock means. In case of an engaged engagement lip the compressibility of the hollow element is neutralized again so that a usual rigid implant results.

Bone splinters or bone replacement material can easily be filled into the interior space of the frontally and backwardly open hollow element and the implant securely be mounted with little operating steps.

To advance a quick ingrowing of the bone the implant is suitably provided with perforations preferably in the form of longitudinal apertures. The longitudinal apertures allow a control of the ingrowing of the bone by means X-ray images in case of a material which is not permeable for X-rays.

For the improvement of the stability of position of the implant the upper and /or lower bone-contact face is provided with a three dimensional texture preferably in the form of longitudinal grooves.

Compared to the prior art the following further advantages of the implant according to the invention accrue:

security against slipping;

improved permeability for X-rays; and enhanced elasticity of the implant.

The invention and further embodiments of the invention are discussed in more detail in the following by means of the partially schematic representations of an embodiment of the invention.

DETAILED DESCRIPTION OF THE PREFERRED EMBODIMENTS

Figure 1:
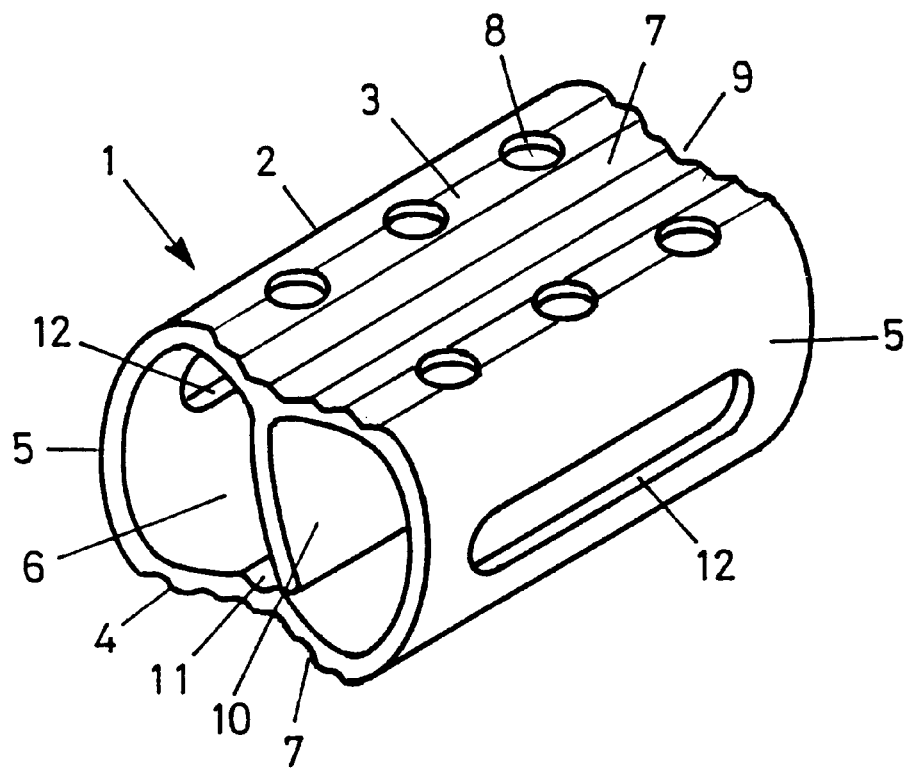
FIG. 1 a perspectival representation of the implant according to the invention in the compressible state with a loose engagement lip.
Figure 2:
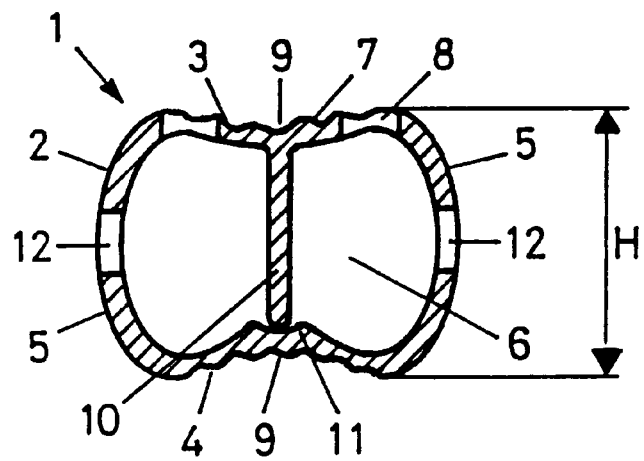
FIG. 2 a cross-section through the implant according to FIG. 1 in the non-compressible state with engaged engagement lip.

The intervertebral implant shown in FIG. 1 and 2 consists essentially of a hollow element 1 in the shape of a hollow cylinder whose outer surface 2 consists of a flattened upper bone-contact face 3, a flattened lower bone-contact face 4 and two lateral faces 5.

The implant may be fabricated in a suitable metal (i.e. titanium), but particularly also in a synthetic material tolerated by the body like polyethylene.

The upper and the lower bone-contact faces 3 and 4 are elastically compressible towards the interior space 6 of the hollow element 1, such that the maximum distance H between the upper and the lower bone-contact face 3 and 4 is reducable, typically by 2 mm. This renders possible an easy insertion of the implant into the intervertebral space.

The lateral faces 5 are provided with recesses in the shape of longitudinal holes 12, which may be omitted when using a synthetic material. The upper bone-contact face 3 and/or the lower bone contact-face 4 is provided with perforations 8 as well as with a central groove 9.

In the interior space 6 of the hollow element 1 an engagement lip 10 is provided, which is engageable in an interlock means 11.

In the following the clinical application is described in detail. The hollow element 1 shown in FIG. 1 is grasped at by means of a suitable compression tool, such that a force of pressure, typically 12 Newton, may be applied on the upper and the lower bone-contact faces 3 and 4 which compresses the hollow element 1. In this state the implant is inserted into the emptied intervertebral space as ever possible without distraction tools whereby the three dimensional textures 7 in the shape of longitudinal grooves facilitate the leading of the implant and offer a protection against a possible slipping.

The compression tool is removed and the engagement lip 10 is set upright and engaged into the interlock means 11 such that the hollow element 1 is not compressible any longer. The implant may now be filled with bone splinters or bone replacement material.

What is claimed is:

1. An intervertebral implant comprising a flattened shaped hollow element defining an interior space within an outer surface that includes a generally flattened upper bone-contact face, a generally flattened lower bone-contact face spaced by a maximum distance H from the upper bone-contact face and two lateral faces, wherein the upper and lower bone-contact face are elastically compressible towards the interior space of the hollow element such that the maximum distance H between the upper and lower bone-contact face is reducible by 0.5 to 5.0 mm and wherein the interior space is open at anterior and posterior ends.

2. The implant according to claim 1, wherein the lateral faces have an arcuate shape and the maximum distance H between the upper and lower bone-contact faces is reducible by 1–3 mm.

3. The implant according to claim 1, wherein a force of pressure of 12 Newton on the upper and lower bone-contact faces reduces the maximum distance H by 15% to 30%.

4. An intervertebral implant comprising a flattened shaped hollow element defining an interior space within an outer surface that includes a generally flattened upper bone-contact face, a generally flattened lower bone-contact face spaced by a maximum distance H from the upper bone-contact face, two lateral faces, an engagement lip provided within the interior space of the hollow element, and an interlock means provided within the interior space of the hollow element, wherein the upper and lower bone-contact face are elastically compressible towards the interior space of the hollow element such that the maximum distance H between the upper and lower bone-contact face is reducible by 0.5 to 5.0 mm, and wherein said interlock means and engagement lip are configured and dimensioned such that the engagement of the engagement lip with the interlock means prevents the compression of the upper and lower bone-contact faces.

5. The implant according to claim 1, wherein the lateral faces are provided with elongated apertures to promote the formation of new bone.

6. The implant according to claim 1, wherein at least one of the bone-contact faces is textured to stabilize the implant.

7. The implant according to claim 1, wherein at least one of the bone-contact faces is provided with perforations to promote bone ingrowth.

8. The implant according to claim 1, wherein at least one of the bone-contact faces is provided with at least one central groove to facilitate compression of the implant.

9. The implant according to claim 1, wherein the implant is made of a biocompatible plastic material.

10. The implant according to claim 1, wherein the implant is coated with an hydroxylapatite of tricalciumphosphate (TCP).

11. The implant according to claim 1, wherein the hollow element has the shape of a hollow cylinder, hollow truncated cone, hollow truncated pyramid, or hollow truncated wedge.

12. The implant according to claim 6, wherein both bone-contact faces are textured.

13. The implant according to claim 7, wherein both bone-contact surfaces include perforations.

14. The implant according to claim 8, wherein both bone-contact faces include a central groove to facilitate compression of the implant.

15. The implant according to claim 9, wherein the implant is made of polyethylene.

16. An intervertebral implant comprising a hollow support member that defines an interior space within an outer surface that includes a generally flattened first bone-contact face, a generally flattened second bone-contact face, and a pair of lateral faces having an arcuate shape and connecting the first and second bone-contact faces at a maximum distance H therebetween, wherein the support member is made of a biocompatible material which is sufficiently resilient to allow the first and second bone-contact faces to be elastically compressible towards each other in the interior space upon the application of force thereto to reduce the maximum distance H, with the bone-contact faces attempting to return to their original configuration when the force is removed and wherein the interior space is open at anterior and posterior ends.

17. An intervertebral implant comprising a hollow support member that defines an interior space within an outer surface that includes a generally flattened first bone-contact face, a generally flattened second bone-contact face, a pair of lateral faces having an arcuate shape and connecting the first and second bone-contact faces at a maximum distance H therebetween, an interior wall extending from the first bone-contact face toward the second bone-contact face through the interior space, and interlock means associated with the second bone-contact face for receiving the wall, wherein the support member is made of a biocompatible material which is sufficiently resilient to allow the first and second bone-contact faces to be elastically compressible towards each other in the interior space upon the application of force thereto to reduce the maximum distance H, with the bone-contact faces attempting to return to their original configuration when the force is removed and wherein engagement of the wall and the interlock means after the bone contact faces return to their original configuration prevents further compression of the first and second bone-contact faces.

18. The implant according to claim 16, wherein at least one of the bone-contact or lateral faces includes an aperture to promote bone ingrowth, and at least one of the bone-contact faces includes a texture to stabilize the implant and at least one central groove to facilitate compression of the implant.

19. The implant according to claim 16, wherein the support member has the shape of a hollow cylinder, hollow truncated cone, hollow truncated pyramid, or hollow truncated wedge, and is made of a plastic material so that the maximum distance H is reduced by at least 15% when the bone-contact surfaces are compressed.

* * * * *